United States Patent [19]

Zelman

[11] 4,306,556
[45] Dec. 22, 1981

[54] METHOD AND APPARATUS FOR STORING AND PREPARING CRYOPRESERVED BLOOD

[75] Inventor: Allen Zelman, Troy, N.Y.

[73] Assignee: Rensselaer Polytechnic Institute

[21] Appl. No.: 119,423

[22] Filed: Feb. 7, 1980

[51] Int. Cl.³ .............................................. A61J 1/00
[52] U.S. Cl. .............................. 128/272; 128/214 D
[58] Field of Search ............. 128/214 D, 214 R, 272, 128/DIG. 24, 213 A, 213 R; 210/22 A

[56] References Cited

U.S. PATENT DOCUMENTS

| | | | |
|---|---|---|---|
| 4,132,594 | 1/1979 | Bank et al. | 128/272 |
| 4,152,184 | 5/1979 | Bacehowski | 128/272 |
| 4,222,379 | 9/1980 | Smith | 128/272 |

OTHER PUBLICATIONS

"Evaluation of Hemodialyzers and Dialysis Membranes", DHEW Publication No. (NIH) 77-1294, Klein et al., 1977.

Primary Examiner—Robert W. Michell
Assistant Examiner—Thomas J. Wallen
Attorney, Agent, or Firm—McGlew and Tuttle

[57] ABSTRACT

A bag for containing blood or blood components comprising a closed container made of material which is permeable to a cryoprotective agent, such as glycerol, which may be added to the blood or blood components directly through the permeable walls of the blood bag. The cryoprotective agent protects the blood or blood components when the blood is frozen for storage and the cryoprotective agent can thereafter be removed through the permeable walls of the container without contaminating the blood therein. An apparatus and process is also disclosed for the cryoprotective agent to be added or removed from the blood bag using electric current, hydrostatic pressure, centrifugal force or osmosis.

8 Claims, 7 Drawing Figures

METHOD AND APPARATUS FOR STORING AND PREPARING CRYOPRESERVED BLOOD

FIELD AND BACKGROUND OF THE INVENTION

The present invention relates in general to the preservation of blood and, in particular, to a new and useful method and apparatus for storing and preparing cryopreserved blood particularly red blood cells.

The supply, storage and use of blood or components thereof poses various and long standing problems in the field of medicine. While large quantities of blood or its components are always in demand, the requirements are sporadic and unpredictable so that large quantities must be stored and maintained at various locations such as blood banks and large hospitals. While such quantities must always be maintained and held ready, a standing problem exists particularly with the storage of red blood cells, in that the red blood cells and other blood components are highly perishable. One very important solution in preserving blood has been the development of techniques in freezing red blood cells or whole blood to preserve them for long periods of time. To prevent the destruction of the red blood cells while they are being frozen, it has been found necessary to add a cryopreserving agent to the blood. When the blood is to be used, after it has been thawed, this cryopreserving agent must be washed out of the blood. The usual agent used is glycerol at a concentration of between about 40 to 50%. With the use of such high amounts of glycerol, the rate of freezing or thawing has not been found to be critical and storage of the blood or red blood cells is at between $-60°$ C. to $-80°$ C. Storage can be in liquid nitrogen, liquid nitrogen vapor or achieved by mechanical refrigeration devices or dry ice. The blood has been found to be stable even with rises in the storage temperature so that the so preserved blood can be transported in dry ice to areas of consumption.

While the blood stored in high concentrations of glycerol is relatively insensitive to temperature changes, the concentration of glycerol itself has posed a problem in that it must be somehow removed before the blood is used. In one example, it has been found necessary to use no less than seven dilution and sedimentation cycles over a period of hours in order to remove the glycerol from the blood or red blood cells which have been frozen in 40% glycerol. This process known as deglycerolization, was improved somewhat by the introduction of an agglomeration process by which the red blood cells could be sedimented without the use of a centrifuge device.

An improvement in the above method of freezing blood or red blood cells came with the introduction of a technique using relatively low concentrations of glycerol. It was found that the concentration of glycerol could be reduced to approximately 20% which permitted deglycerolization in three or four sedimentation cycles in a clinical centrifuge with the process time reduced to one or two hours. The reduction in glycerol concentration, however increased the sensitivity of the blood to temperature changes so that the blood preserved by this method required storage and transportation in liquid nitrogen or liquid nitrogen vapor. It was found that even transient rises in the storage temperature led to extreme hemolysis of the red blood cells.

Some of the problems outlined above in removing the cryoprotective agent from the blood have been solved by the introduction and use of cell washing devices which are capable of automatically processing large quantities of blood. The cost of such units is high, however, and is only economical when large quantities of blood are available to be processed.

Additional problems in removing the cryopreserving agent from frozen blood or red blood cells is the possible introduction of contaminants since, at some point in the known processes, the blood is brought into direct contact with washing solutions and the like which must be supplied from some source external to the container in which the blood was collected and stored. Another problem in using frozen blood is the relatively long time period which is required to render the blood usable, that is deglycerolized. Especially when the blood is used in small institutions such as hospitals located at remote areas, an emergency situation requiring unexpected large quantities of blood cannot be treated effectively since the time lag required in processing the frozen blood would be prohibitive. Another problem existing where emergencies are anticipated and large quantities of blood are prepared is that the frozen blood once thawed and deglycerolized has a life of only about 24 hours. If for some reason the emergency fails to materialize, the blood must either be used elsewhere within the 24 hours or else it is outdated and no longer useful. It must also be noted that the blood must be matched to potential donors so that this reduces further the number of potential recipients which can use the thawed blood. This loss of otherwise useful blood is particularly onerous in view of the difficulty in obtaining and maintaining sufficient blood supplies throughout the United States. The discovery and use of a technique of thawing and deglycerolizing frozen bood or red blood cells in a relatively short period of time would be particularly useful not only in permitting the emergency use of frozen blood but would also enhance the inventory control of blood since frozen blood can be stockpiled in periods of high availability and then selectively used in periods of shortage.

SUMMARY OF THE INVENTION

The present invention is drawn to a process and apparatus for adding or removing the cryoprotective agent from blood preserved by freezing and particularly frozen red blood cells.

A blood bag is used which has walls made of a material which is permeable to glycerol. Once the bag is sterilized and supplied with blood from a donor, the steps of glycerolizing, freezing and deglycerolizing the blood may be performed without any direct contact with the interior of the bag so that a sterile condition can always be maintained, and no conditions are provied to endanger the sterile condition. This may substantially extend the post-thaw useful life of the blood or red blood cells since the known post-thaw life of 24 hours is established due to the danger of contamination from bacterial or virol growth after this period.

The invention is also drawn to an apparatus for processing the blood or red blood cells stored in the glycerol permeable bag and to a process of glycerolizing and deglycerolizing blood or red blood cells so stored. It has been found that glycerolization and deglycerolization through the permeable wall of the blood bag can be achieved either by electoosmotic transfer of the glycerol into or out of the bag or by applying a hydrostatic pressure which drives fluid through the bag carrying glycerol into or out of the bag, or by using a centrifugal force to drive fluid through the bag thereby carrying glycerol into or out of the bag, or an osmotic gradient which would drive fluid through the bag and carry glycerol into or out of the bag. The characteristics of the material used for the blood bag walls, in addition to their being highly permeable to glycerol, are that the material be resistant to fracture in its frozen state, it be flexible, sterilizable, preferably transparent for the visual inspection of the blood or blood cell condition and that it have minimal leaching of plasticizers. These criteria are met by several materials for example the polycarbonate membrane developed for the NIH used in hemodialysis and manufactured by American Membrane, Inc. Membranes can now be manufactured both highly permeable and sufficiently strong that the membrane material itself could be used to form the blood bag. For example, a prototype blood bag made from polycarbonate membrane and filled with blood (300 ml) was dropped 4 ft. to the floor several times without breaking the bag. However, it may also be found useful to seal the polycarbonate membrane directly to an electroosmosis membrane. Electroosmosis membranes are generally about 0.5 mm thick with a nylon backing so that they can withstand severe trauma. With either blood bag, the blood or red blood cells should only come in contact with a non-ionic membrane with a blood compatibility similar to the polycarbonate or Cuprophane membranes used for example during hemodialysis.

Polycarbonate membranes of the described type are freezable to $-80°$ C. in 4 moles of glycerol without cracking. The bags are also highly permeable to glycerol and have high tear resistance and can also be heat-sealed for the convenient formation of the blood bags. The blood bags may be formed, for example, with one or two ports to permit the connection of an infusion set. Integrated tubing may also be provided to permit collection of blood from a donor and for the transfer of bood to satellite packs and the like. This permits a system of collection, freezing with glycerolization, storage, deglycerolization and readministration using a single bag system.

Since the membranes used to form the bags are also usually highly permeable to water, to improve handling characteristics, it has been found advantageous to place the membrane bag into an additional plastic container which is not permeable to water. The additional plastic bag would, of course, be removed during deglycerolization.

Examples of the use of electric fields on blood samples concerning electrodialysis of blood can be found in the following articles:

Bier, M., Brucker, G. C. and Roy, H. E., "Blood Electrolysis", *Trans. Am. Soc. Artif. Int. Organs*, 13:227 (1967);

Smith, A. L., Berkowitz, H. D. and Bluemle, L. W., "Electrodialysis of Blood: Evaluation of a High Capacity Unit", *Trans. Am. Soc. Artif. Int. Organs* 10:273 (1964);

Adachi, R., "The Studies on the Jikei Electrodialyzer", Report VII, *Acta Aurol.*, 7:274 (1961);

Berkowitz, H. and Bluemle, L. W., "Electrodialysis of Blood: Some Problems and Approaches to Their Solution", *Trans. Am. Soc. Artif. Int. Organs*, 9:97 (1963).

From these studies, it has been found that the electrodialysis of blood does not cause direct damage to the corpuscular elements of the blood such as the red blood cells. The reason for this appears to be the high electrical resistance of the cell walls of these elements which prevents the passage of electrical current therethrough. There has also been found to be no loss of biological activity of the proteins exposed to the electrical current as demonstrated in the article "Preparative Electrophoresis Without Supporting Media", Bier, M., *Electrophoresis*, Academic Press Inc., New York (1959).

Accordingly, an object of the present invention is to provide a bag for containing blood or blood components and in particular red blood cells comprising a closed container having at least one port for the entry and exit of blood and at least one wall portion which is permeable to a cryoprotective agent whereby the cryoprotective agent can be removed or added to the blood through said at least one wall portion without removing the blood from the container or breaking sterility.

Another object of the present invention is to provide a process for removing or adding a crypoprotective agent to blood or blood components which is to be or has been frozen, providing a container for the blood and cryoprotective agent mixture having at least one wall which is permeable to the cryoprotective agent, and exposing the container to an electric field for causing the active movement of the cryoprotective agent through the wall portion and out of or into the container and blood mixture.

A still further object of the present invention is to provide a process for adding or removing a cryoprotective agent from blood or blood components which is to be or has been frozen in a mixture with the cryoprotective agent comprising, providing a container for the blood and cryoprotective agent mixture having at least one wall portion which is permeable to the cryoprotective agent, and providing a hydrostatic pressure difference across the permeable wall for forcing the cryoprotective agent through the wall portion and out of, or into said container.

A still further object of the present invention is to provide a process for adding or removing a cryoprotective agent from blood or blood components which is to be or has been frozen in a mixture with the cryoprotective agent comprising, providing a container for the blood and cryoprotective agent mixture having at least one wall portion which is permeable to the cryoprotective agent, and providing a centrifugal force to at least one side of the container for forcing the cryoprotective agent through the wall portion and into or out of said container.

A still further object of the present invention is to provide a process for adding or removing a cryoprotective agent from blood or blood components which is to be or has been frozen in a mixture with the cryoprotective agent mixture having at least one wall portion which is permeable to the cryoprotective agent, and providing osmotic pressure to at least one side of the container for forcing the cryoprotective agent through the wall portion and into or out of said container.

Another object of the present invention is to provide an apparatus for removing, or adding a cryoprotective agent to blood which has been or is to be frozen in a mixture with the cryoprotective agent comprising, a housing having a blood mixture chamber adapted for containing the mixture of blood and cryoprotective agent in the blood bag and a wash solution chamber, a partition in said housing separating said blood mixture chamber from said wash solution chamber having at least one wall portion which is permeable to the cryoprotective agent but not to at least one component of the blood, wash solution supply and discharge means connected to said wash solution chamber for renewing a supply of wash solution therein, and cryoprotective agent transport means connected across said wall portion for forcing the cryoprotective agent therethrough and out of or into said blood mixture chamber.

A still other object of the present invention is to provide an apparatus for removing or adding a cryoprotective agent from blood wherein the transport means for forcing the cryoprotective agent through the wall portion comprises an electrode positioned on either side of said wall portion and electric field means connected to said electrodes for establishing an electric field therebetween and across said wall portion to force the cryoprotective agent thereacross by electro-osmosis.

A still further object of the present invention is to provide an apparatus for adding a cryoprotective agent, or removing the same from blood or blood components wherein the cryoprotective agent transport means comprises means for establishing hydrostatic pressure on one side of said wall portion for forcing the cryoprotective agent into or out of the blood bag.

A still further object of the present invention is to provide an apparatus for a cryoprotective agent to be added or removed from blood or blood components wherein the cryoprotective agent transport means comprises means for establishing a centrifugal force on one side of said wall portion for forcing the cryoprotective agent into or out of the blood bag.

A still further object of the present invention is to provide a blood bag design and apparatus therefor to remove a cryoprotective agent from the blood or add the agent to the blood which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
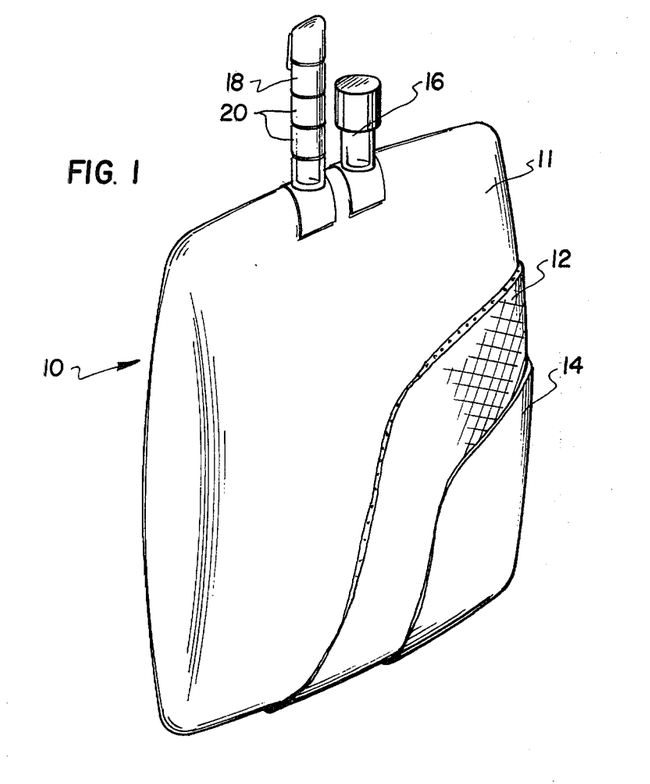
FIG. 1 is a perspective view of the blood bag constructed in accordance with the invention.

Referring now to the figures in particular, the invention embodied therein, FIG. 1 comprises a blood bag generally designated 10 for containing whole blood or components thereof, particularly red blood cells. In accordance with the invention, the blood or red blood cells are mixed with a cryoprotective agent which is usually glycerol solution. The entire bag is then quick-frozen using, for example, liquid nitrogen or mechanical freezing units which is a known technique for preserving and storing the blood or blood components for future use. In accordance with the invention, the blood bag includes at least one wall portion which is permeable to the cryoprotective agent, in this case, glycerol. While only a portion of the bag 10 need be permeable, it is preferable to have the entire bag wall 11 which comes into contact with the blood made of the glycerol permeable material. An example of material which is permeable to glycerol while being capable of retaining red blood cells and excluding contaminants such as bacteria and the like is a polycarbonate membrane for hemodialysis manufactured by American Membrane, Inc. While the wall 11 could itself form the bag, it is advantageous to seal the permeable wall 11 to a reinforcing membrane 12 which may include nylon threads extending therethrough. An example of material which can be used for this reinforcing wall is a suplonated polystyrene electro-osmosis membrane. Since the membranes 11 and 12 are also permeable to water, an outer plastic container or bag 14 may be provided into which the blood bag comprising walls 11 and 12 may be placed for storage and handling. When the cryoprotective agent is to be removed from bag 10 in accordance with the invention, however, this outer impermeable bag 14 is removed. The reinforcing wall and outer bag 12 and 14 are shown in section but where such layers are used, it is understood that they totally encompass the inner permeable wall 11.

The blood bag 10 is also advantageously provided with a port fitting 16 which is adapted for receiving blood from a donor in known fashion, for receiving the cryoprotective agent and, when the blood is to be dispensed, for supplying the blood to a recipient. A second port fitting 18 may be provided which may include a plurality of sectional chambers 20 which may be filled with blood from bag 10 and, in the frozen state, removed one at a time for typing purposes. The blood contained in bag 10 can therefore be typed for certain factors without invading the body of bag 10 and also without requiring the blood to be thawed.

Figure 2:
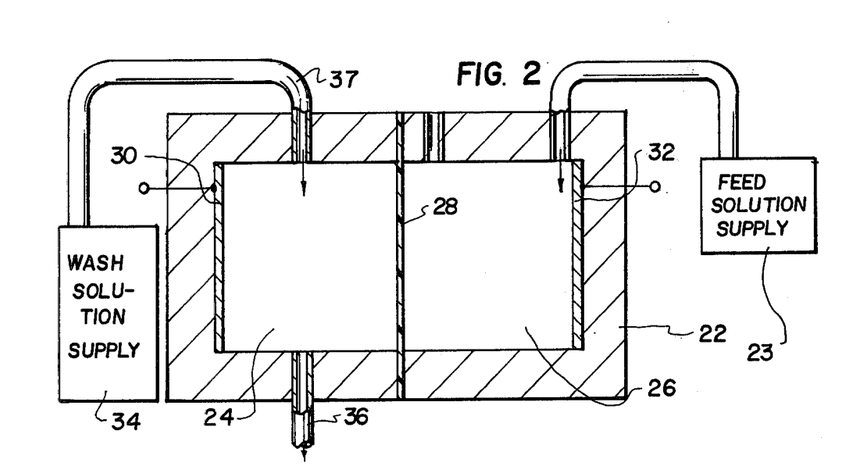
FIG. 2 is a side sectional view of a two-component system for removing cryoprotective agent from blood in accordance with the invention.

With reference to FIG. 2, the principles of electroosmosis as used in accordance with the invention will be described. Electroosmosis is the process by which a solution can be transferred through convection as a result of an electric current flow. Ionic polymer membranes notably have high electro-osmotic activity. The electric current applied across such a membrane travels primarily by counter ions. Molecular collisions between these counter ions and the solution, drive the solvent in the direction of the electric current. If the solvent is bound directly to these counter ions, this will increase the total solvent transfer through the membrane. Therefore, if any non-electrolytes are present and permeable to the membrane, they will be transferred through convection with the solvent. Electrolytes which are present, however, will not be transferred as a result of socalled Donnan exclusion from the membrane. Electroosmosis thus leads to an efficient and active separation of non-electrolytes from electrolytes.

Turning to FIG. 2, a two-component chamber 22 is shown having a wash solution compartment 24 and a blood mixture compartment 26 divided by a permeable membrane 28. Electrodes 30 and 32 are provided in the respective compartments and energized with a programmable current supply. It has been found that the use of alternating current rather than direct current is preferable since direct current leads to concentration polarization at the solution-membrane interface, that is the region of the respective compartments immediately adjacent the membrane 28.

The use of alternating current at selected frequencies removes the polarization concentration each time the current reverses its direction. Alternating current alos permits the use of reversible electrodes since depletion during one cycle of the current is replenished during the following cycle. The use of reversible electrodes eliminates pH changes and the evolution of gas. While the embodiment of the invention shown in FIG. 2 can be used for deglycerolizing blood in chamber 26, a problem of dehydration arises since the flow of water out of the blood in chamber 26 is not compensated. An electrolyte or wash solution supply means 34 is connected through a line 27 to the wash solution or electrolyte chamber 24 and continually drained through a drain 36. Glycerol and water forced through membrane 28 is thus continually washed from the chamber 24. Chamber 26 containing the blood mixture is analogous to an electrolyte plus non-electrolyte mixture chamber. The blood fluid can be maintained by a feed solution supply 23. For glycerolizing the blood, supply 34 can provide the agent rather than wash it away.

Details of the electro-osmosis process when applied generally to the transfer of non-electrolytes is disclosed in an article entitled "Rapid Filtration of Non-Electrolytes by Electro-osmosis", A. Zelman, D. Walsh, H. Wayt and D. Gisser (1978).

Figure 3:
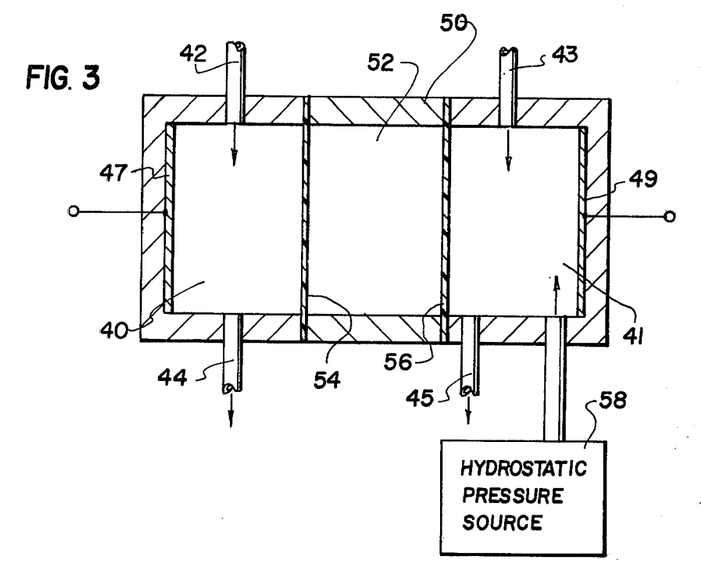
FIG. 3 is a side sectional view of a three-component system used in accordance with the invention.

Turning to FIG. 3, the problem of dehydration of the blood or blood components is solved by providing a three-compartment chamber 50 having two compartments 40 and 41 for containing the wash or electrolyte solution each supplied with electrolyte or wash solution from an apparatus similar to wash solution supply means 34 through lines 42 and 43. The solutions are continually drained through drain lines 44 and 45. First and second electrodes 47 and 49, respectively, are provided in the compartments 40 and 41 and can be supplied with electricity through their terminals by a programmable current supply. Between compartments 40 and 41 is a central blood mixture compartment 52 which is defined between first and second membranes 54 amd 56, respectively.

According to one method of the invention, the two membranes 54 and 56 may be of the same ionic character so that dehydration of the blood within compartment 52 is avoided. FIG. 3 shows the use of a pair of cation exchange membranes 54 and 56. When the current supplied to the electrodes is such to make electrode 47 an anode and electrode 49 a cathode, the electric current flows from electrode 47 through the two cationic membranes 54 and 56 and to the electrode 49. Concurrently with this current flow, a total volume flux or flow of equal magnitude is established across member 54 from compartment 40 to compartment 52 and across membrane 56 from compartment 52 to compartment 41.

Since the glycerol will follow with the current, glycerol or any other cryoprotective agent in the blood contained in compartment 52 will move from that compartment into the solution wash compartment 41 whereas water alone will flow from compartment 40 into compartment 52.

When the current is reversed, making electrode 47 a cathode and electrode 49 an anode, current will flow to the left as seen in FIG. 3 across the membranes 54 and 56 and again glycerol will leave compartment 52 and enter compartment 40 while an equal volume of water will enter compartment 52 through membrane 56.

According to another object of the invention, the electrodes 47 and 49 may be excluded or not energized and the function replaced by hydrostatic pressure, centrifugal force or osmotic pressure means to force fluid through the blood bag. Either of these means alone can be relied on to force water from compartment 41 to the blood mixture compartment 52 and, to maintaining equilibrium, to force glycerol from compartment 52 to compartment 40. Simultaneously with this application of pressure, compartment 40 is continually washed of glycerol through the lines 42 and 44.

Figure 4:
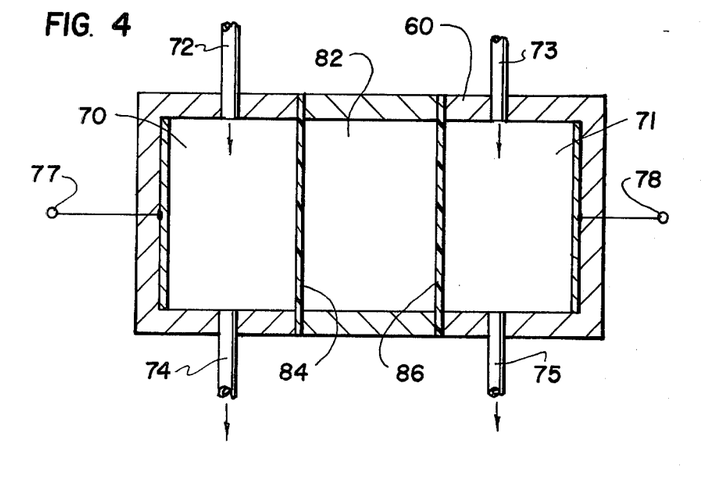
FIG. 4 is a view similar to FIG. 3 illustrating the current and material flow through the system when the electric field applied to the electrodes thereof is reversed with respect to that applied to the apparatus of FIG. 3.

Turning to FIG. 4, an alternate method of removing glycerol or other cryoprotective agent from the cryopreserved blood is shown. In this embodiment of the invention, a three-component chamber 60 is provided which has electrolyte or wash solution compartment 70 and 71 which are supplied with wash solutiions through lines 72 and 73 which solution is continuously drained through drain lines 74, 75. A pair of electrodes 77, 78 are provided in these compartments and connected to a programmable current supply for supplying a current across membranes 84 and 86 which define therebetween a blood mixture compartment 82. In accordance with this embodiment of the invention, the membrane 84 is a cation exchange membrane and the membrane 86 is an anion exchange membrane. The wash or electrolyte solutions supplied to compartments 70 and 71 contain, for example, NaCl. When electric current passes from left to right as shown in FIG. 4 so that electrode 77 acts as anode and electrode 78 acts as cathode, Na ions being positive will pass into compartment 82 from the left-hand compartment 70 and Cl ions being negative will pass from the right-hand compartment 71 into the central compartment 82. This will cause a forced change in the concentration gradient between the red blood cell and its external solution. The cell will shrink forcing glycerol out of the red blood cell into the solution.

When the current is reversed making electrode 77 the cathode and electrode 78 the anode, the negative Cl ions will leave compartment 82 through the anode membrane 86 and positive Na ions will leave compartment 82 through the cathode membrane 84. During this half cycle, water and glycerol will be removed from the extra cellular fluid of the blood in compartment 82. The lowering of centration in the fluid surrounding the red blood cell causes the cells to swell.

If the second cycle above described is permitted to proceed until the removal of salt from the water causes the red blood cells to swell, and the next cycle adds sufficient salt to compartment 82 to cause the cells to shrink, pumping of the glycerol from the red blood cells will occur. By ending the cycle with the same volume as originally contained in chamber 82, one is assured of a proper electrolyte balance.

Since the frequency of the alternating current as well as the magnitude thereof can be easily adjusted through a programmable current supply, the rate of glycerol addition or removal can be completely automated in any of the methods illustrated in FIGS. 3 or 4.

It should be noted that glycerol should not be removed too quickly in the initial stages of deglycerolization since a danger exists that the red blood cells will swell and hemolyze. Thus, during the beginning stages of deglycerolization using the inventive method and apparatus, the current is supplied at low levels and gradually increases as the glycerol concentration of the cells decreases. Frequencies of between 0.001 to 0.1 Hz are useful in practicing the invention and the magnitude of current should be variable in time between about 1–75 ma/cm$^2$.

Figure 5:
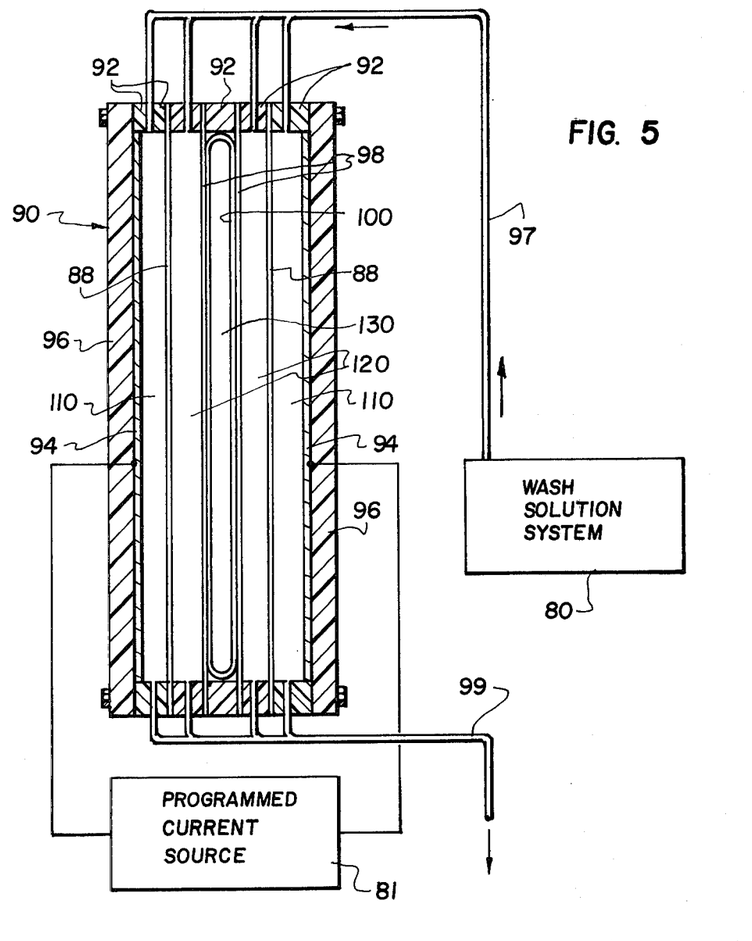
FIG. 5 is a side sectional view of an apparatus in accordance with the invention for processing blood contained in the blood bag illustrated in FIG. 1.

Turning to FIG. 5, additional apparatus in accordance with the invention are shown which comprise a five-compartment chamber generally designated 90 made of two Plexiglass plates 96, 96 each having an electrode 94 thereon separated by five rubber spacers 92. The electrode plates 94 used in an experiment conducted in accordance with the invention had dimensions of 21 cm by 10 cm and the assembly was bolted together to form the five compartments. Between the five spacers 92 were positioned two electrodialysis membranes 88, 88, and two electro-osmosis membranes 98, 98 which, together defined two electrode wash compartments 110, two dialysate compartments 120 and one blood bag compartment 130 into which was positioned a blood bag 100 having a wall made of polycarbonate membrane. Wash solution in the form of a dialysate was supplied from wash solution system or means 80 through a line 97 to each of the dialysate and electrode wash compartments 110 and 120. This wash solution was continuously removed through a drain line 99. The electrodes were energized by programmable current source 81. For additional details concerning the electrodialysis technique, the types of dialysates used and the materials for forming the electrodialysis membranes see the article "Blood Electrodialysis" cited above. In compartments 110 and 120 isotonic NaAC (sodium acetate) was circulated while compartments 130 contained glycerolized blood in bag 100. Alternating electric current was then applied to the electrode 94. The frequencies used were 0.0017 Hz, 0.0033 Hz, 0.0067 Hz and 0.033 Hz. Current densities were adjustable from 0 to 50 ma/cm$^2$.

The central compartment solution containing blood had a glycerol concentration of 3.54 M to start. At the end of the experiment the blood was analyzed for glycerol using osmometry. The difference in the osmolality between the blood before and after deglycerolization gave the number of moles of glycerol removed from the blood.

Glycerol transfer was found to vary both with frequency and current density. For all frequencies and current densities tested, the total glycerol transfer remained greater than that which would be caused by diffusion alone.

The results are summarized in Tables I - III.

Table I represents the data on the % deglycerolization as a function of time for 23.8 ma/cm$^2$ and 0.0067 Hz AC. Each line in these tables represents a new blood sample, therefore there is biological variability in this data as well as experimental error.

TABLE I

| time (min) | Δosm mOsm | n$_t$ in (moles) | Δn$_t$ (moles) | % deglycercolization |
|---|---|---|---|---|
| 0 | 0 | .460 | 0.000 | 0.0 |
| 5 | 958 | .460 | .144 | 31.3 |
| 10 | 771 | .496 | .131 | 26.4 |
| 15 | 1167 | .460 | .175 | 38.0 |

Δosm represents change in osomolality of blood sample
n$_t$ in represents total number of moles of glycerol initially
Δn$_t$ represents change in the total number of moles of glycerol.

Table II represents the data on the % deglycerolization as a function of current density for different switching frequencies.

TABLE II

| Freq (Hz) | Current density (ma/cm$^2$) | Δosm (mOsm) | n$_t$ in (moles) | Δn$_t$ (moles) | % deglycerolization |
|---|---|---|---|---|---|
| | 0 | 86 | 1.240 | .030 | 2.4 |
| | 14 | 1304 | .425 | .156 | 36.8 |
| .0017 | 24 | 2564 | .425 | .188 | 44.2 |
| | 34 | 1620 | .708 | .324 | 45.8 |
| | 44 | 1340 | .708 | .268 | 44.9 |
| | 0 | 86 | 1.24 | .030 | 2.4 |
| .033 | 24 | 381 | 1.77 | .191 | 10.8 |
| | 48 | 172.5 | 2.00 | .097 | 4.9 |

Table III represents the data on the % deglycerolization as a function of frequency.

TABLE III

| Freq. (Hz) | Δosm (mOsm) | n$_t$ in (moles) | Δn$_t$ (moles) | % deglycerolization |
|---|---|---|---|---|
| 0.0017 | 1564 | .425 | .188 | 44.2 |
| 0.0033 | 993 | .425 | .119 | 28.0 |
| 0.0067 | 959 | .460 | .125 | 27.1 |
| 0.033 | 381 | 1.77 | .191 | 10.18 |

Since the wash solution from means 80 never comes into direct contact with the blood in blood bag 100, it need not be subject to stringent sterile conditions which substantially reduces the costs thereof so that it can economically be continually washed through the chambers 110 and 120.

Figure 6:
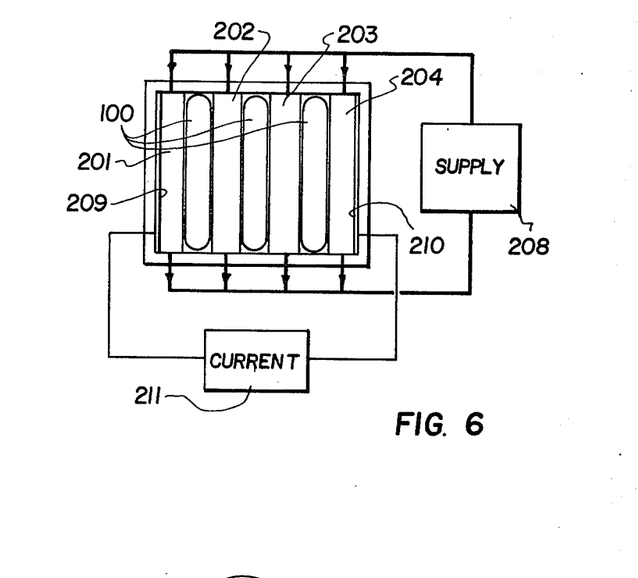
FIG. 6 is a schematic side elevational view of an apparatus for processing a series of blood bags in accordance with the invention.

In FIG. 6, a plurality of devices similar to the arrangement shown in FIG. 5 are assembled in series. The blood bags 100 are flanked by chambers 201, 202, 203, and 204 which can be supplied with washing solution from washing solution system 208. A pair of electrodes 209 and 210 are disposed on opposite ends of the respective end chambers 201 and 204 and supplied with programmed current from a programmed current source 211. Only a single programmed current source 211 need be provided which forms the cryoprotective agent forcing means to treat the plurality of blood bags 100 in series. It is understood that the means 211 can be replaced by hydrostatic pressure means or osmotic pressure means or the entire arrangement can be mounted to impart a centrifugal force on the arrangement to move the cryoprotective agent in accordance with the invention.

Figure 7:
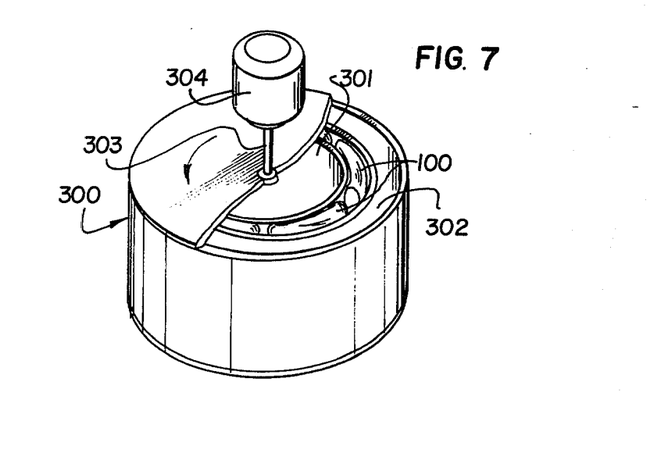
FIG. 7 is an illustrative perspective view of a centrifugal force apparatus in accordance with the invention.

FIG. 7 shows a simplified form of an apparatus used to practice the invention which comprises a carousel 300 for supporting one or more blood bags 100. Carousel 300 includes an inner chamber 301 and an outer chamber 302. Carousel 300 is mounted for rotation on shaft 303 and rotated by motor means 304 in known fashion. Inner chamber 301 can be supplied with a washing solution or cryoprotective agent solution depending on whether the bags 100 are to be treated with the cryoprotective agent or cleansed of the cryoprotective agent. When motor means 304 rotates carousel 300, centrifugal force is produced forcing the fluid from chamber 301 into and through the bags 100 and into the outer chamber 302.

Although frozen, deglycerolized red cells are now generally available in large urban hospitals and through regional blood centers, because of the high cost of the procedure, this product is generally used only for special applications. Frozen red cells are generally not available in rural communities, third world nations, or in small military installations because of the technical demands of the procedure. The present invention offers the possibility of a system requiring minimum technician involvement, fully automated processing equipment, a system in which the cells remain within a single container throughout the entire sequence of glycerolizing, freezing, deglycerolizing and administration, and a system in which the processing bag is never entered, thus permitting an extension of the restrictive 24-hour outdating period.

The introduction of a method of storing cells at $-20°$ C. eliminates the need for expensive and specialized storage facilities. Only the cost and clumsiness of deglycerolization stands in the way of cost-effective use of frozen cells for other than special applications. The inventive method provides a rapid, safe, effective and economical deglycerolizing procedure. The electro-osmotic preparation of blood cells of the invention is especially suited for automation. Thus, less technical expertise will be required and there will be less chance for error. For these reasons, cryogenically preserved cells can be made available to rural regions.

The number of units to be processed simultaneously is essentially without limit and it is unimportant how many patients receive these units.

In emergency situations several units of blood may have to be processed simultaneously for a single individual or several units may have to be processed simultaneously for several individuals. Present methods of cell washing from a single bowl are laborious, slow and in principle hazardous due to the possibility of contamination. The electro-osmotic processing of frozen cells is intrinsically simple in these situations. The blood processor can be designed in stacks so that the current passes through each blood bag simultaneously. Each bag is self-contained, sterile and can be washed in series with other bags with no possibility of cross contamination.

While specific embodiments of the invention have been shown and described in detail to illustrate the application of the principles of the invention, it will be understood that the invention may be embodied otherwise without departing from such principles.

What is claimed is:

1. A bag for containing a mixture of blood or blood components and a cryoprotective agent and, in particular red blood cells, comprising a container having at least one port for the entry and exit of blood or blood components and at least one semi-permeable wall portion which is permeable to the cryoprotective agent whereby the cryoprotective agent can be added to or removed from the container through the wall portion, the wall portion being made of dialysis membrane of the type used in hemodialysis.

2. A bag for containing blood or blood components according to claim 1, wherein said at least one wall portion comprises the entire container.

3. A bag for containing blood or blood components according to claim 1, further including reinforcing strands associated with said at least one wall portion to strengthen it.

4. A bag for containing blood or blood components according to claim 1, wherein said at least one wall portion comprises a polycarbonate membrane.

5. A bag for containing blood or blood components according to claim 4, further including reinforcing strands associated with said membrane.

6. A bag for containing blood or blood components according to claim 1, further including reinforcing strands extending through said electro-osmosis membrane.

7. A bag for containing blood or blood components according to claim 1, further including a removable outer water-impervious plastic bag around said closed container.

8. A bag for containing a mixture of blood or blood components and a cryoprotective agent and, in particular, red blood cells, comprising a container having at least one port for the entry and exit of blood or blood components and at least one semi-permeable wall portion which is permeable to the cryoprotective agent and whereby the cryoprotective agent can be added to or removed from the container through the wall portion, an electro-osmosis membrane connected to an exterior of at least one wall portion whereby the cryoprotective agent can be added to or removed from the closed container through said at least one wall portion and said electro-osmosis membrane by the passage of an electric current through said at least one wall portion and electro-osmosis membrane.

* * * * *